US012640261B2

(12) United States Patent
Neuhaus

(10) Patent No.: US 12,640,261 B2
(45) Date of Patent: May 26, 2026

(54) MEDICAL DEVICE, SYSTEM OF MEDICAL DEVICES, AND METHOD FOR CONFIGURING A MEDICAL DEVICE

(71) Applicant: WEINMANN EMERGENCY MEDICAL TECHNOLOGY GMBH + CO. KG, Hamburg (DE)

(72) Inventor: Christian Neuhaus, Quickborn (DE)

(73) Assignee: WEINMANN EMERGENCY MEDICAL TECHNOLOGY GMBH + CO. KG, Hamburg (DE)

( * ) Notice: Subject to any disclaimer, the term of this patent is extended or adjusted under 35 U.S.C. 154(b) by 130 days.

(21) Appl. No.: 18/283,298

(22) PCT Filed: Mar. 1, 2022

(86) PCT No.: PCT/DE2022/100170
§ 371 (c)(1),
(2) Date: Sep. 21, 2023

(87) PCT Pub. No.: WO2022/199745
PCT Pub. Date: Sep. 29, 2022

(65) Prior Publication Data
US 2024/0177847 A1     May 30, 2024

(30) Foreign Application Priority Data

Mar. 26, 2021    (DE) ..................... 10 2021 107 674.9

(51) Int. Cl.
G16H 40/40              (2018.01)
(52) U.S. Cl.
CPC .................................. G16H 40/40 (2018.01)

(58) Field of Classification Search
CPC ........ G16H 40/40; G16H 20/30; G16H 20/40; G16H 40/63
See application file for complete search history.

(56) References Cited

U.S. PATENT DOCUMENTS 8,051,414 B2 * 11/2011 Stender .................. G16H 40/40
717/168
2008/0295839 A1 * 12/2008 Habashi ............ A61M 16/0051
128/204.22

(Continued)

FOREIGN PATENT DOCUMENTS

AU          726792 B2 * 10/1998
DE    102017202821 A1    8/2018
DE    102019129606 A1    5/2020

OTHER PUBLICATIONS

Srinivasan et al. "A rapidly deployable individualized system for augmenting ventilator capacity." Science Translational Medicine. vol. 12, No. 549. Jun. 24, 2020. (Year: 2020).*

(Continued)

*Primary Examiner* — Linh Giang Le
(74) *Attorney, Agent, or Firm* — LUCAS & MERCANTI, LLP; Klaus P. Stoffel

(57)            ABSTRACT

A medical device, a system of medical devices, and a method for configuring a medical device, in which the control of at least one medical device can be configured by the operator or the user of the medical device by a suitable user interface for adapting or newly creating specific operating modes, more particularly for adapting the operating modes to changed guidelines or to individualized guidelines.

10 Claims, 3 Drawing Sheets

(56) References Cited

U.S. PATENT DOCUMENTS

2009/0281598 A1* 11/2009 Haubrich ............... G16H 40/67
607/60
2018/0238984 A1    8/2018 Paul
2018/0317826 A1* 11/2018 Muhsin .............. A61B 5/14552

OTHER PUBLICATIONS

International Search Report Dated May 31, 2022, PCT/DE2022/
100170, 2 Pages.

* cited by examiner

FIG.3 opening a configuration module on a medical device selecting an existing operating mode of the medical device or a new operating mode to be created detecting inputs of a user for selecting functional elements to be used for the operating mode of the medical device, for configuring the sequence of the functional elements used and/or the parameters of individual functional elements of the operating mode storing the user inputs as a configuration of an existing operating mode or as a new operating mode

MEDICAL DEVICE, SYSTEM OF MEDICAL DEVICES, AND METHOD FOR CONFIGURING A MEDICAL DEVICE

CROSS-REFERENCE TO RELATED APPLICATIONS

The present application is a 371 of International application PCT/DE2022/100170, filed Mar. 1, 2022, which claims priority of DE 10 2021 107 674.9, filed Mar. 26, 2021, the priority of these applications is hereby claimed and these applications are incorporated herein by reference.

BACKGROUND OF THE INVENTION

The invention relates to a medical device, for example, within the meaning of a ventilator or a defibrillator.

Furthermore, the invention relates to a system of medical devices, wherein at least one of the medical devices is designed as a ventilator or as a defibrillator.

In addition, the invention relates to a method for configuring a medical device.

The guidelines applicable to the ventilation and/or the defibrillation of a patient, for example, in the context of a cardiopulmonary resuscitation, are already implemented with the aid of corresponding medical devices or the implementation thereof is assisted by the output of instructions by a medical device to a human helper.

The implementation of the guidelines is partially different from city to city, however. In addition, requirements differing from one another for the configuration of such a medical device exist in various applications of the corresponding medical devices. Thus, for example, armies have different requirements than a civil emergency service.

It is therefore not possible to develop a medical device, whether a ventilator, a defibrillator, or a system of medical devices, for example, including a ventilator and a defibrillator, which has a configuration matching with all applications.

The prior art is to be able to perform options or settings on the medical devices, so that minor adjustments of the control of the respective medical device are possible. However, if a more extensive change or adjustment is required, new firmware has to be created to implement this changed configuration using a medical device. Such new firmware also requires, in addition to the investments accompanying the development as such, a renewed authorization, which is also time-consuming and costly. In particular for smaller applications, such an adjustment of the control of the respective medical device or system by new firmware to the solution matching best medically according to the respective guidelines is not cost-effectively implementable, however.

SUMMARY OF THE INVENTION

It is therefore an object of the invention to provide a medical device on which individual modes or processes are configurable by an operator or user of the medical device, without new device software having to be developed and uploaded.

A further object of the invention is to provide a system of medical devices in which individual modes or processes are configurable by an operator or user of the system of medical devices, without new device software having to be developed and uploaded onto at least one medical device of the system.

A further object of the invention is to specify a method for configuring a medical device which enables the configuration of new modes or processes of the control of a medical device by an operator or user of the medical device without new device software having to be developed and uploaded.

The features of a medical device and a system of medical devices disclosed hereinafter are part of the invention both individually and in all implementable combinations.

A medical device according to the invention includes at least one display, one input device, one storage device, and one control unit.

The display is also used, in addition to displaying possibly detected vital parameters of a patient and information on the respective operating mode of the medical device, for displaying a graphical user interface, referred to hereinafter as a "GUI" (graphical user interface), which is usable for configuring the process of the control of the medical device in individual operating modes of the medical device.

The input device is used to detect user inputs, in particular also with respect to the configuration of the process of the control of the medical device, and in embodiments of the invention includes one or more buttons, switches, or rotary switches, or is additionally or exclusively designed as a touch input of the display.

Depending on the embodiment of the medical device, it furthermore includes a therapy module, which is designed for the therapeutic treatment of a patient.

In advantageous embodiments of the invention, the medical device includes a monitoring module, which is used for detecting and/or monitoring at least one vital parameter of a patient and/or at least one device-related measured value.

In embodiments of the invention, the medical device includes an acoustic output device, which is designed for acoustic output of instructions to a human helper and/or for acoustic output of alarms.

In embodiments of the invention, the medical device additionally includes at least one optical output device in addition to the display, which is designed for output of optical signals, in particular for optical output of alarms.

In one embodiment of the invention, the optical output device is designed as at least one light, which lights up in color to output an alarm signal.

Alternatively or additionally to the optical output device, however, optical alarms can also be output via the display in embodiments of the invention.

A medical device according to the invention enables its operator or user to configure separate modes for controlling the medical device.

An operator of a medical device within the meaning of this document is, for example, an emergency service or a hospital. A user of a medical device within the meaning of this document is, for example, an emergency medical technician or paramedic of an emergency service.

A mode is in this case a process of the control of the medical device, wherein the control of the medical device is defined by the sequential and/or parallel execution of functional elements.

In a medical device designed as a ventilator, such a mode is given, for example, by "IPPV" (intermittent positive pressure ventilation), in which the ventilation is executed using intermittent positive pressure. This is a volume-controlled form of the ventilation using a ventilator.

The mode includes various functional elements which are given in the example "IPPV", inter alia, by "activation of the fan", "pressure measurement", "evaluation of the measurement data", and "alarm".

Further functional elements within the meaning of this document are, for example, the detection of a measured value, the output of instructions or suggested actions to a human helper (optical and/or acoustic), the activation of a machine assistance (for example, thorax compression device during a CPR), and the output of measured values (e.g., digitally, acoustically, or as a printout with the aid of an integrated or separate printer).

The functional elements of a mode are generally parameterized, so that the manner of the actual implementation of the respective functional element is configurable via one or more parameters.

In the example "IPPV", the following parameters are assigned to the corresponding functional elements: tidal volume (Vt), ventilation frequency (f), positive end-expiratory pressure (PEEP), maximum inspiration (pMax), and pressure the inspiration-expiration ratio (I:E). Therefore, configurable ventilation modes, a process control, a guideline assistance, a free selection of the settable parameters, and/or possible setting ranges for parameters with respect to preprogrammed modes are provided for a user of a medical device according to the invention.

The configurability of a medical device or a system of medical devices according to the invention is therefore enabled by providing the possibilities of selecting functional elements, defining the sequence of the functional elements, and/or setting the parameters of the individual functional elements for an individual operating mode.

In one preferred embodiment of the invention, all three above-mentioned possibilities of the configuration are provided jointly.

For example, individual modes for supraglottic intubated patients or for desaturated COPD patients may thus be configured freely or on the basis of predetermined modes by an operator or a user of a medical device according to the invention.

In one embodiment of the invention, a configuration of a mode or the selection of specific parameters or settings on the medical device is also considered, for example, after a machine-assisted anamnesis of a patient.

In one embodiment of the invention, a user interface for graphic or programming language-based configuration of the medical device is provided by the GUI. For example, a configuration by programming in XML is possible.

In embodiments of the invention, the definition of decision trees, guidelines, or expert systems is also possible by the configuration.

The adaptation of the control of the medical device in a defined mode is therefore carried out in embodiments of the invention by the performance of a configuration by the operator or user of the medical device on the medical device itself and not by uploading adapted firmware.

In one embodiment of the invention, the GUI of the medical device includes free "slots" for the storage and the selection of such individual modes.

In one particularly preferred embodiment of the invention, the medical device includes a tool for graphic programming of the modes, so that the configuration of individual modes is also assisted by persons who have not mastered a classic programming language.

In one embodiment of the invention, a medical device or a system of medical devices is configurable like a tree. Within the meaning of this document, this means that a configurable parameter is linked to one or more subordinate parameters, which are configurable as a whole or partially.

In one embodiment of the invention, the parameters assigned to a functional element are automatically configured to standard values in the selection and arrangement of the functional element in the process of a mode.

In advantageous embodiments of the invention, if at least one subordinate parameter is assigned to a configurable parameter, the at least one subordinate parameter is also configured to a standard value upon a configuration of the configurable parameter. The value of the at least one subordinate parameter is, if it is a configurable subordinate parameter in this case, adaptable if needed.

In advantageous embodiments of the invention, dependent parameters are defined, the setting values of which mutually influence one another, i.e., when one parameter is changed, the possibly existing at least one dependent parameter is also automatically changed according to a saved rule.

For example, the modes and parameters mentioned hereinafter are selectable and/or configurable for medical devices according to the invention designed as ventilators or defibrillators.

Conceivable modes for a ventilator are, for example, IPPV, aPCV (assisted pressure control ventilation) possibly in conjunction with ASB (assisted spontaneous breathing), PRVC (pressure regulated volume control) possibly in conjunction with ASB, bilevel possibly in conjunction with ASB, PCV, SIMV (synchronized intermittent mandatory ventilation) possibly in conjunction with ASB, S-IPPV, CPAP (continuous positive airway pressure) possibly in conjunction with ASB and CCSV (chest compression synchronized ventilation).

The aPCV mode is used for the pressure-controlled assisted ventilation at a fixedly set mandatory ventilation frequency. If spontaneous breathing is present, the patient has the option of increasing the frequency and thus the minute volume. If the patient displays a spontaneous respiratory effort within a specific time window, the mandatory ventilation breath is synchronized with the breathing of the patient. The time window or trigger window can be set in % of the expiration time ($T_e$) before the next mandatory ventilation breath to be expected. If the patient displays a spontaneous respiratory effort outside the set trigger window, no mandatory ventilation breath is triggered. The following ventilation can parameters be configured in this mode:

pInsp: inspiration pressure
Freq.: ventilation frequency
PEEP: positive end-expiratory pressure
pMax: maximum inspiration pressure
InTr: inspiratory trigger
I:E: inspiration-expiration ratio The controlled-assisted ventilation mode PRVC+ASB unifies the advantages of pressure-controlled and volume-controlled ventilation. The set tidal volume is applied using the least possible ventilation pressure. The ventilation begins with three volume-controlled breaths having the set tidal volume. The device selects the measured plateau pressure as the starting value for the inspiration pressure pInsp of the following pressure-controlled ventilation. It measures the administered volumes and adjusts the ventilation pressure. If the lung parameters change during the ventilation, the device changes the inspiration pressure pInsp in steps of at most 3 mbar in order to reach the set tidal volume again and thus automatically compensate for changes on the patient. The measurement of the applied volume is improved by a compensation of the hose compliance. The desired tidal volume is thus precisely controlled in particular at small tidal volumes under high airway pressures. The set maximum pressure limit (pMax) ensures the safety of the patient. For safety reasons, the inspiration pressure pInsp is 5 mbar below the set maximum pressure limit (pMax). If this inspiration pressure (pInsp=pMax−5 mbar) should be reached, the device administers as much volume as possible. If this volume deviates from the set tidal volume, the device triggers the moderate priority alarm "Vt not reachable". The following ventilation parameters can be configured in this mode:

Vt: tidal volume (breath volume)
Freq.: ventilation frequency
PEEP: positive end-expiratory pressure
pMax: maximum inspiration pressure
ΔpASB: pressure assistance (relative to the set PEEP)
InTr: inspiratory trigger
ExTr: expiratory trigger
I:E: inspiration-expiration ratio The bilevel+ASB mode is used for the pressure-controlled ventilation combined with free spontaneous respiration at the pressure level pInsp and PEEP during the entire respiration cycle and settable pressure assistance at PEEP level. This mode is used in patients without spontaneous respiration or in spontaneously-breathing patients. The patient can trigger a mandatory, pressure-regulated ventilation breath during a defined trigger window. The trigger window is 20% of the expiration time $T_e$ before the mandatory ventilation breath to be expected. During the remaining time, the patient can breathe spontaneously or with the aid of pressure assistance. Tidal volumes and minute volumes result from the set pInsp, the lung compliance, and the set inspiration time Ti. The following ventilation parameters can be configured in this mode:

pInsp: inspiration pressure
Freq.: ventilation frequency
PEEP: positive end-expiratory pressure
pMax: maximum inspiration pressure
ΔpASB: pressure assistance (relative to the set PEEP)
InTr: inspiratory trigger
ExTr: expiratory trigger
I:E: inspiration-expiration ratio The PCV mode is used for the mandatory, pressure-controlled ventilation at fixed pressure levels. This mode is used in patients without spontaneous respiration. A spontaneously breathing patient can breathe through freely during the expiration, however. The set maximum pressure limit (pMax) ensures the safety of the patient. The following ventilation parameters can be configured in this mode:

pInsp: inspiration pressure
Freq.: ventilation frequency
PEEP: positive end-expiratory pressure
pMax: maximum inspiration pressure
I:E: inspiration-expiration ratio SIMV is a ventilation form in which a fixed minimum frequency, but at the same time a ventilation frequency expandable by intrinsic respiration, is specified. The machine ventilation breaths are synchronized here with the spontaneous respiration. The following ventilation parameters can be configured in this mode:

Vt: tidal volume
Freq.: ventilation frequency
PEEP: positive end-expiratory pressure
pMax: maximum inspiration pressure
I:E: inspiration-expiration ratio The mode SIMV+ASB is used for volume-controlled ventilation having fixed mandatory minute volume (MV). The patient can breathe spontaneously between the mandatory ventilation breaths and thus increase the minute volume. If spontaneous respiration is present, the mandatory ventilation breath is synchronized with the respiration of the patient. The mandatory minute volume and the mandatory respiratory frequency remain unchanged here. The set maximum pressure limit (pMax) ensures the safety of the patient. The ventilation mode SIMV+ASB is also used as a mode for apnea ventilation. The patient can trigger a mandatory, pressure-regulated ventilation breath during a fixed trigger window. The trigger window is available in the last 20% of the expiration time $T_e$. During the remaining time, the patient can breathe spontaneously or can breathe spontaneously with the aid of a pressure assistance. The following ventilation parameters can be configured in this mode:

Vt: tidal volume
Freq.: ventilation frequency
PEEP: positive end-expiratory pressure
pMax: maximum inspiration pressure
ΔpASB: pressure assistance (relative to the set PEEP)
InTr: inspiratory trigger
ExTr: expiratory trigger
I:E: inspiration-expiration ratio The S-IPPV mode is a volume-controlled ventilation mode having variable mandatory minute volume (MV). During the entire expiration phase, a trigger is active which enables the patient to trigger a renewed ventilation breath. The patient thus has the option of increasing the respiration frequency and therefore the minute volume MV and adjusting it to his demands. In general, this mode is used in patients having inadequate spontaneous respiration. The ventilation in the mode S-IPPV corresponds to the ventilation in the mode IPPV with the difference that a synchronization with the inhalation efforts of the patient is possible. Due to the lower set respiratory frequency, the patient can trigger spontaneous mandatory ventilation breaths. A trigger window, which extends over the entire expiration time, is available for the synchronization. The following ventilation parameters can be configured in this mode:

Vt: tidal volume
Freq.: ventilation frequency
PEEP: positive end-expiratory pressure
InTr: inspiratory trigger
pMax: maximum inspiration pressure
I:E: inspiration-expiration ratio CPAP ventilation is a form of ventilation which combines the spontaneous respiration of the patient using a continuous overpressure (PEEP) maintained during inhalation and exhalation.

In the CCSV mode, the ventilation breath is triggered synchronously with each thorax compression. Gas volume thus cannot escape from the lungs and the elevated pressure in the lungs ensures a stronger compression of the heart during the cardiac massage. A frequency tachometer helps the user to maintain the optimum compression frequency in this case. One advantage of CCSV is that the ventilation mode can be used with mechanical thorax compression devices.

The monitoring of at least one vital parameter of a patient can be both an independent process, which can be defined, for example, by the functional elements "reading out of a sensor", "processing of the measured values", and "outputting of the measured values" in sequential sequence, or can be part of a process in a specific mode, for example, in the course of ventilation and/or defibrillation. The monitoring may be parameterized, for example, by the vital parameter or parameters to be detected, the sampling frequency, and the form of the output (for example, display of a measured value or output of a diagram having a curve over time).

In the inhalation mode, a patient can be supplied with a constant oxygen volume flow via a loose breathing mask or nasal cannula, but spontaneously breathes on their own.

A further mode configurable in embodiments of the invention is pre-oxygenation, in which a prophylactic enrichment of oxygen in the lungs of a patient is performed before an induced respiratory arrest (apnea), for example, in the scope of a narcosis. For this purpose, inter alia, the oxygen source of a medical device designed as a ventilator is activated so that the oxygen content of the breathing air supplied to a patient is produced with pure or nearly pure oxygen. The patient breathes freely in this case and the ventilator or the fan of the ventilator is only activated for compensation of the hose system. A timer preferably increments the time of the intervention here and this value is displayed to the user of a corresponding device.

In the context of the monitoring of at least one vital parameter of a patient or of device-related data, alarms are configurable in embodiments according to the invention of a medical device, which are triggerable, for example, by exceeding or falling below predetermined and possibly configurable threshold values.

Such alarms are coupled, for example, to one or more of the following parameters: F high, F low (measured value of the respiratory frequency of the patient), PAW high, PAW low (PAW: pressure airways, airway pressure measured at the distal end or patient valve), CO2 high, CO2 low, Vt high, Vt low, hands-off (time of the interruption of a cardiac massage), CPR frequency high, CPR frequency low, apnea (respiratory arrest), patient-side leak, O2 concentration high, O2 concentration low, battery of a medical device weak, remaining runtime of O2 short (oxygen source of the ventilator), input pressure low, oxygen overdose, temperature of the medical device (device hot, device cold), input voltage of the medical device low, input voltage of the medical device high.

The setting of the parameters can be carried out in embodiments of the invention by a free configuration of the user or within predetermined value ranges.

In embodiments of the invention, it can be defined by the operator of a medical device in an expanded configuration mode, which is protected by a password, for example, which parameters are permanently set and which parameters are possibly to be configurable for a user and possibly whether the configuration for a user can take place freely or within predetermined value ranges.

Settable parameters of the various functional elements of the modes are, for example, the inspiration pressure (pInsp), the positive end-expiratory pressure (PEEP), the respiratory frequency or ventilation frequency, the tidal volume (Vt), delta P-ASP, the end-inspiration pause, the ramp of the inspiration, the ramp of the expiration, the curve shape (decelerating flow yes/no), the inspiration trigger, the expiration trigger, the trigger steps, the I/E ratio, and the maximum pressure (pMax).

In the event of an inspiration trigger or an expiration trigger, the inhalation or exhalation effort of a patient is triggered (for example, on the basis of a volume flow measurement or pressure measurement and exceeding or falling below a corresponding threshold value). A ventilator or in particular the fan of a ventilator for assisting the respiration of a patient is activatable on the basis of such a trigger.

If the medical device is designed as a defibrillator, the following modes are selectable and/or configurable in embodiments of the invention: monitoring, cardiac pacemaker (pacing), cardioversion (producing the normal sinusoidal cardiac rhythm), and defibrillation (to be triggered manually).

Settable parameters for the modes of a medical device designed as a defibrillator are in embodiments of the invention:

The charge (corresponding to the energy of the shock), frequency, and the synchronization source of a cardioversion. For an operator, it is pre-determinable with respect to the parameters in embodiments of the invention whether they are settable by a user (yes, no). Furthermore, it is possible for a user to specify an actual value and to specify maximum and/or minimum of the setting range for a parameter.

Further functional elements having possibly assigned parameters (indented) are, in embodiments of the invention:

ECG forwarding
    automatic
    manual
    ECG printing
    data transfer (telemetry)

Further alarms configurable with the aid of a medical device according to the invention are coupled to at least one of the following measured values or state recognized with the aid of the medical device (parameters indented):

asystole
    active
    light active
    acoustic active
    limit/value
    minimum limit
tachycardia (palpitation)
bradycardia (slow heartbeat)
VF/VT
CO2 high
CO2 low
PAO2 low (arterial oxygen partial pressure)
PAO2 high
compression frequency high
compression frequency low
lack of relief CPR
compression depth high
compression depth low
blood pressure high (systolic)
blood pressure low (systolic)
blood pressure high (diastolic)
blood pressure low (diastolic)
temperature (body) high
temperature (body) low As a further functional element, in embodiments of the invention, the view (graphic output of the medical device) is configurable in the meaning that an operator and/or a user can select an individual representation on the display of the medical device for a mode.

In embodiments of the invention, the operator can thus arrange setting fields, measured value fields, curves, and trends as desired on the display, present various preconfigurations for selection to a user, and/or block the change of the layout for the user.

A system according to the invention of medical devices includes at least two of the following medical devices: ventilator, defibrillator, monitor, medical pad. At least one ventilator or one defibrillator is always a part of the system according to the invention of medical devices as a therapeutic medical device here.

A medical pad within the meaning of this document is used to output instructions or, in general, guidelines to be applied for a therapeutic method to a user of a system of medical devices, in particular to a human helper. Additionally or alternatively, the medical pad can be designed for controlling the one ventilator and/or one defibrillator.

A monitor as an independent medical device within the meaning of this document is a medical device for monitoring at least one vital parameter of a patient. However, the monitor can also be part of the ventilator and/or the defibrillator and can possibly be designed for monitoring at least one device-related measured value.

A system of medical devices according to the invention comprises at least one medical device according to the invention according to this document.

The medical devices of a system of medical devices according to the invention are connected to one another to exchange data and/or control signals.

A system of medical devices according to the invention is configurable by inputs on at least one medical device of the system for implementing processes. With the aid of these processes, guidelines for the treatment of patients are also implementable by a system of medical devices according to the invention, which provide the use of multiple different medical devices, for example, a ventilator and a defibrillator for implementing lifesaving measures.

In one preferred embodiment of the invention, one of the medical devices of the medical system is designed as a master, which sends control signals required for implementing a selected process to the at least one further medical device of the system.

In one embodiment of the invention, a medical system includes a ventilator and a defibrillator.

A method according to the invention for configuring a medical device comprises at least the following method steps:

starting a configuration module on a medical device
    selecting an existing operating mode of the medical device or an operating mode to be newly created
    detecting inputs of a user for selecting functional elements to be used for the operating mode of the medical device, for configuring the process of the functional elements used and/or the parameters of individual functional elements of the operating mode with the aid of the medical device
    storing the configuration of an existing operating mode or a new operating mode defined by the user inputs.

The configuration of a medical device or a system of medical devices is used to implement a predetermined process of functional elements. Such functional elements are, for example, the activation of a ventilator and/or a defibrillator or the technical modules for implementing the provided function of the respective medical device. Special modes for the treatment of a patient are implementable by the specific activation of the ventilator and/or the defibrillator.

The individual functional elements can be parameterized here by one or more possibly dependent parameters according to the preceding description of a medical device according to the invention.

With respect to the functional element of the activation of the ventilator, the parameterization is carried out, for example, by the specification of the fan speed, so that the pressure and/or the volume flow of a ventilation as well as the frequency and duration of the ventilation are pre-determinable.

Further parameterizations with respect to the activation of the ventilator are, for example, the state of the valve (open/ closed), the volume flow source (fan and/or external source), and the pressure and/or flow sensors for the patient gas.

With respect to the functional element of the activation of the defibrillator, the parameterization is carried out, for example, by the specification of the number and/or the strength of the shocks (charge) and/or possibly the duration and/or the frequency of the shocks.

With respect to the functional element of the cardiac massage, in the case of a manual cardiac massage, the parameterization is carried out, for example, by the specification of the position, the frequency, the depth, the direction, and/or the relief of the cardiac massage by output of instructions to a human helper and in the case of a machine cardiac massage by a corresponding activation of a device for carrying out a cardiac massage.

The configuration mode is implemented in advantageous embodiments of the invention as software which is installed and executable on the medical device.

In preferred embodiments of the invention, the configuration mode uses the display of the medical device to output information with respect to the configuration or the configurations to a user.

In one embodiment of the method according to the invention for configuring a medical device, the access to an expanded configuration mode, which enables specifications about the scope of the normal configuration mode, is enabled by the input of a password.

In one embodiment of the invention, both the normal configuration mode and the expanded configuration mode are protected by passwords which are different from one another, so that the access to the configuration and the scope of the configuration of the medical device can be reserved for appropriately trained persons.

In one embodiment of the invention, the configuration module is executable independently of the medical device to be configured, for example locally on a PC or in the Internet, and the generated configuration is storable.

The created configuration is tested with the aid of a device simulation in embodiments of the invention.

The generated and tested configuration is in embodiments of the invention either uploaded manually onto at least one medical device or uploaded with the aid of an update server onto a plurality of devices, for example, onto all corresponding devices of an operator which has generated the configuration.

BRIEF DESCRIPTION OF THE DRAWING

Exemplary embodiments of the invention are illustrated in the figures explained hereinafter. In the figures:

FIG. 3: shows a flow chart of a method according to the invention for configuring a medical device.

DETAILED DESCRIPTION OF THE INVENTION

Figure 1:
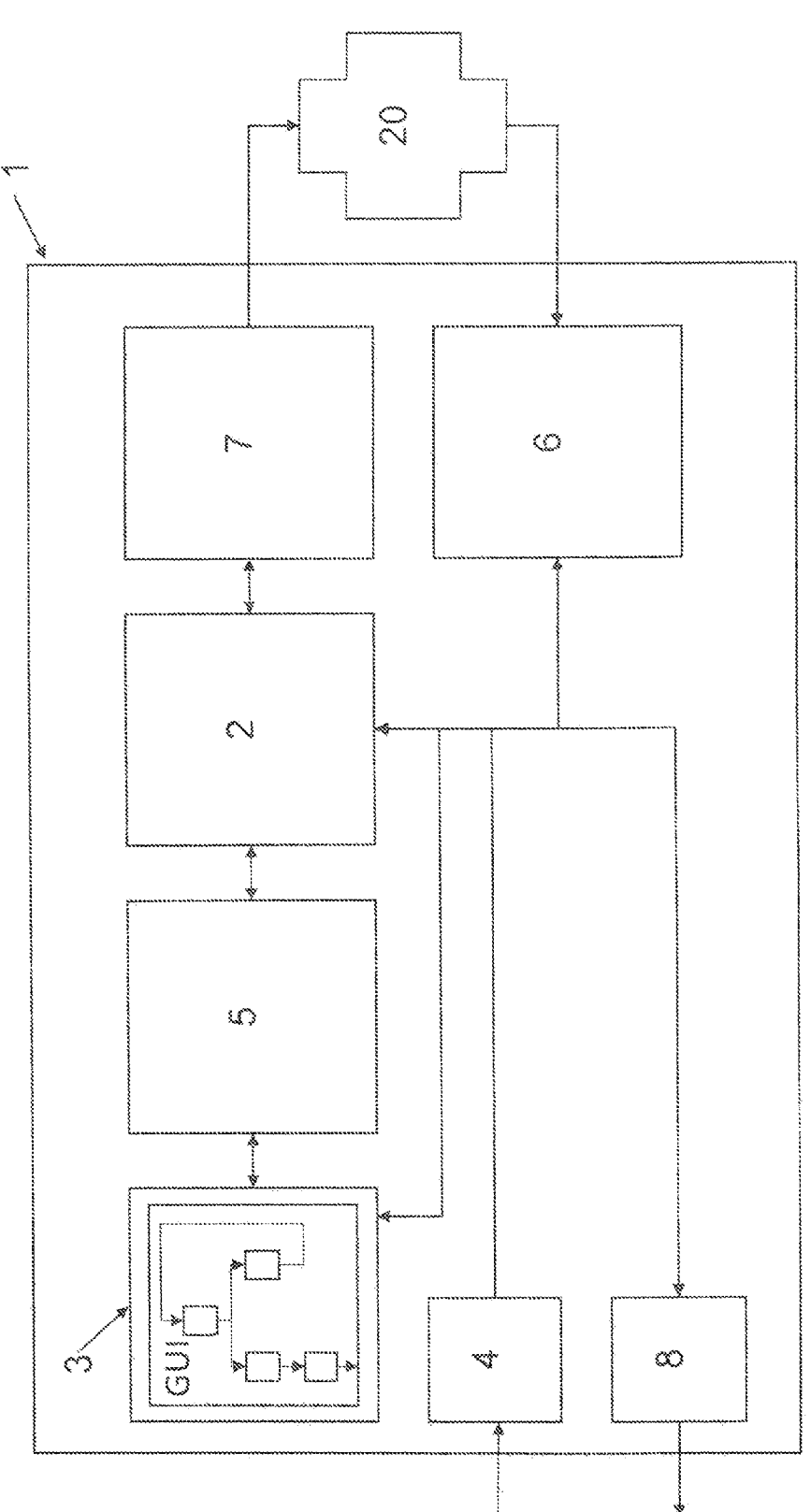
FIG. 1: shows a schematic illustration of the block diagram of a medical device according to the invention.

FIG. 1 shows a schematic illustration of the block diagram of a medical device (1) according to the invention. The medical device (1) includes a control unit (2), using which the process of the control of the medical device (1) is implementable for the various operating modes. Furthermore, the medical device (1) includes a display (3), an input device (4), a storage device (5), a monitor (6), a therapy module (7), and an acoustic output device (8).

The therapy module (7) comprises the units required for the therapeutic treatment of a patient (20) according to the embodiment of the medical device (1). The therapy module (7) of a medical device (1) designed as a ventilator comprises, in embodiments of the invention, for example, a fan having the corresponding power electronics, an oxygen source, a hose system, a ventilation mask, and a volume flow sensor and/or a pressure sensor and possibly a gas sensor (for example CO2 or O2). The therapy module (7) of a medical device (1) designed as a defibrillator, in contrast, comprises a charge storage device, a power electronics unit, and electrodes which are designed to emit shocks to a patient (20).

With the aid of the GUI displayable on the display (3), it is possible for an operator or a user of a medical device (1) according to the invention to adapt existing modes or create new modes by inputs via the input device (4).

A mode thus generated is storable on the storage device (5), so that it is retrievable by the control unit (2) to execute the corresponding mode.

With the aid of the control unit (2), the therapy module (7), the display (3), the acoustic output device (8) and also the monitor (6) and possibly the storage device (5) are activatable to implement the selected mode.

The monitor (6) includes the units required for detecting at least one vital parameter of a patient (20) and/or for detecting at least one device-related measured value.

In one embodiment of the invention, the monitor (6) and/or the therapy module (7) is or are arranged separately from the configurable medical device (1), so that a system of medical devices (10) according to the invention is formed.

Figure 2A:
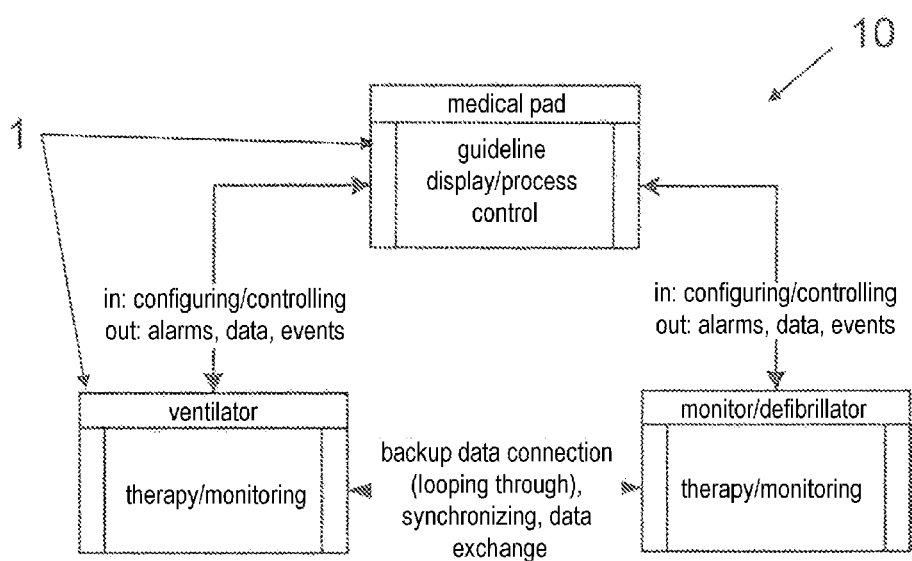
FIGS. 2a-2c: show schematic illustrations of a system of medical devices according to the invention.
Figure 2B:
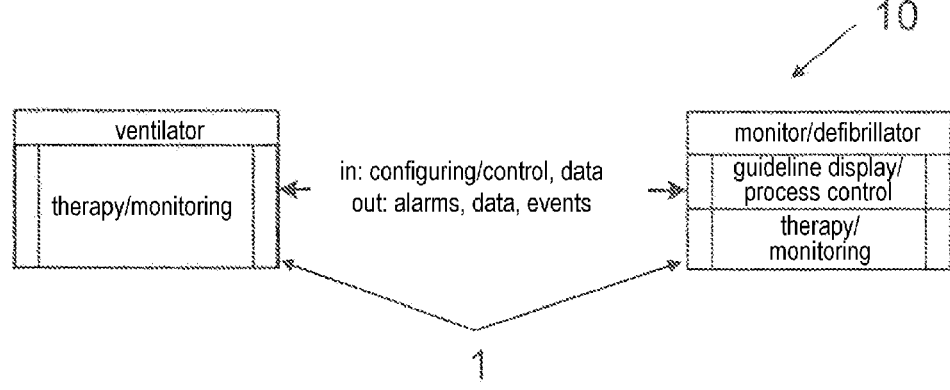
Figure 2C:
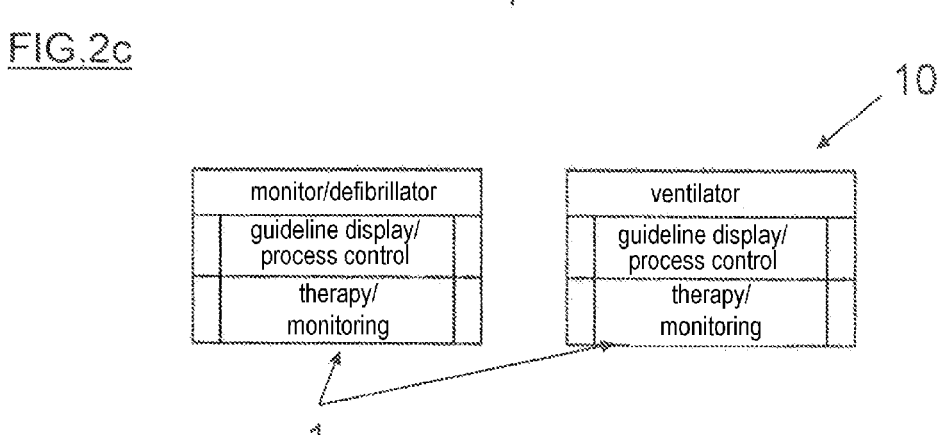

FIGS. 2a, 2b, and 2c show various embodiments of such a system of medical devices (10) according to the invention. In a first embodiment, the system of medical devices (10) includes a medical pad and a ventilator. In a second embodiment, the system of medical devices (10) includes a medical pad and a defibrillator. In a third embodiment, the system of medical devices (10) includes a medical pad, a ventilator, and a defibrillator. This third embodiment is shown in FIG. 2a. In a fourth embodiment, the system of medical devices (10) includes a ventilator and a defibrillator. This embodiment is shown in FIGS. 2b and 2c. In the above-mentioned embodiments of a system of medical devices (10) according to the invention, a standalone monitor (6) can be used in each case alternatively to the defibrillator or additionally. Alternatively, only the monitoring function of a defibrillator can also be used.

The embodiments of a system according to the invention shown in FIGS. 2b and 2c differ in the linkage of the devices. While a communication takes place between the devices in the embodiment according to FIG. 2b, for example, to exchange configuration data or carry out a synchronization, the devices operate independently of one another in the embodiment shown in FIG. 2c.

Figure 3:
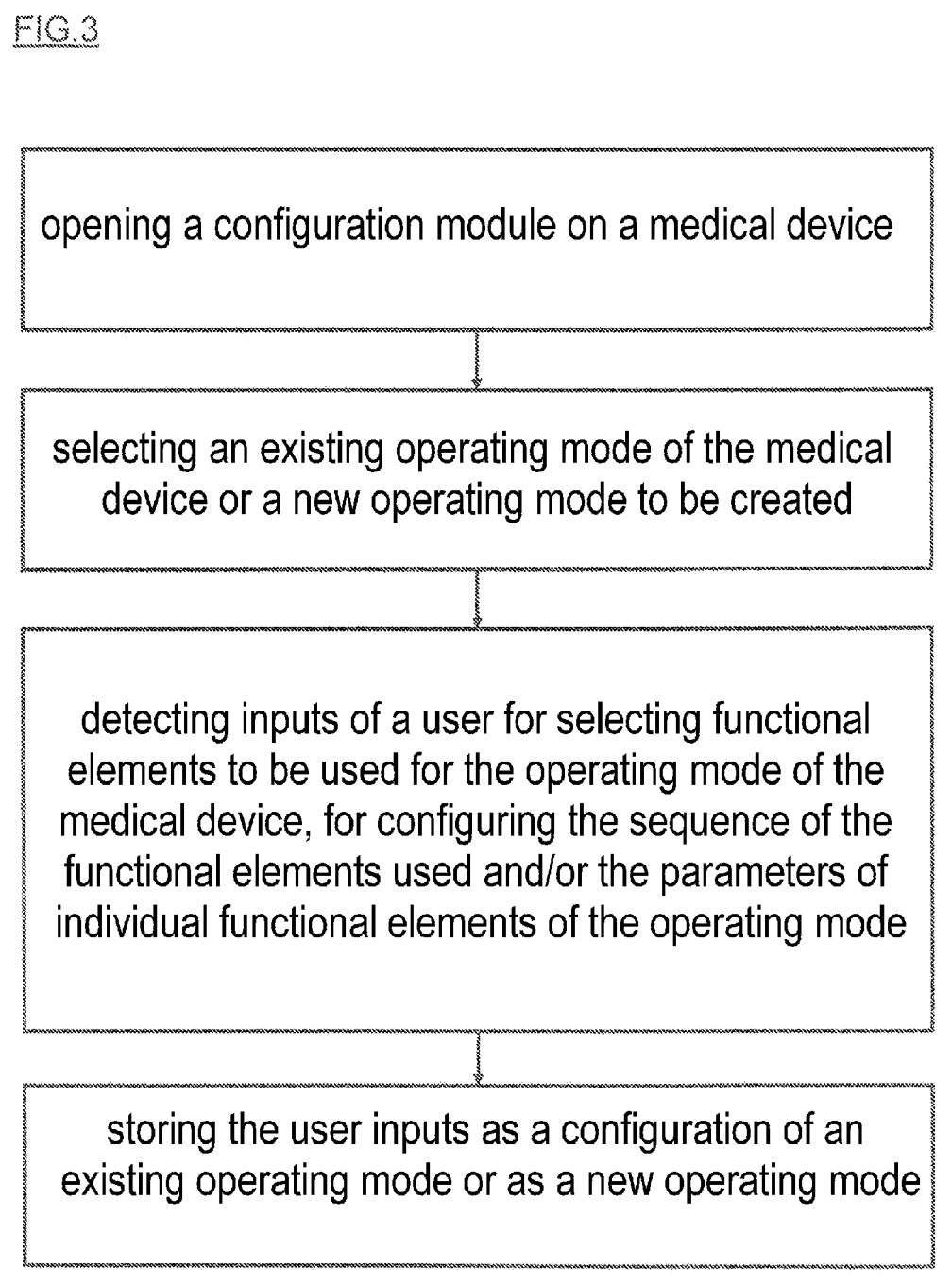

FIG. 3 schematically shows a flow chart of an embodiment of a method according to the invention for configuring a medical device.

The invention claimed is:

1. A medical device, comprising: at least one control unit; a storage device; and a display for displaying a graphic user interface, wherein the medical device is constructed to be configurable by a configuration module that is executable independently of the medical device to be configured, wherein configuring the medical device includes adjusting and/or creating operating modes of the medical device and wherein a process of the control of the medical device is defined in each case by an operating mode, and wherein a configuration created by an operator and tested using a device simulation is loadable onto the medical device manually or by using an update server, wherein the configuration is a declarative configuration (including XML) loadable without rebuilding firmware and executed by a controller of the medical device, and wherein authoring or editing of the sequence of functional elements is performed by the configuration module.

2. The medical device according to claim 1, wherein, by way of the configuration of an operating mode of the medical device, functional elements used in the operating mode and processes of the functional elements used are definable to form a sequence of control of the medical device for the operating mode, wherein the sequence is authored by the configuration module and stored a generated configuration.

3. The medical device according to claim 2, wherein the parameters defining the functional elements used are settable by the configuration of an operating mode of the medical device, including parameter ranges defined in the generated configuration.

4. The medical device according to claim 1, comprising a protected expanded configuration mode in which a type and a scope of settings performable in a normal configuration mode are definable.

5. The medical device according to claim 1, wherein the medical device is a ventilator or a defibrillator.

6. A system of medical devices, comprising at least two medical devices connected to one another to exchange data and/or control signals, wherein at least one of the medical devices is a defibrillator or a ventilator, wherein the at least one medical device is a medical device according to claim 1, wherein a system operating mode authored by the configuration module is loadable onto the medical devices.

7. The system of medical devices according to claim 6, wherein a process of control of the medical devices of the system is definable by a configuration of an operating mode of the system, the system operating mode being authored by the configuration module and defining orchestration and synchronization across the medical devices.

8. A method for configuring a medical device, comprising the steps of:
 starting a configuration module that is executable independently of the medical device;
 selecting an existing mode for configuration or applying a new operating mode;
 configuring a process of functional elements and/or parameters of individual functional elements of the operating mode to author a declarative configuration (including XML); and
 storing the configuration of an existing operating mode or a new operating mode;
 testing the created configuration with a device simulation; and
 loading the created and tested configuration onto the medical device manually or by using an update server without rebuilding firmware.

9. The method according to claim 8, wherein the medical device comprises: at least one control unit; a storage device; and a display for displaying a graphic user interface, wherein the medical device is constructed to be configurable by a configuration module that is executable independently of the medical device to be configured, wherein configuring the medical device includes adjusting and/or creating operating modes of the medical device and wherein a process of the control of the medical device is defined in each case by an operating mode, and wherein a configuration created by an operator and tested using a device simulation is loadable onto the medical device manually or by using an update server, wherein the configuration is a declarative configuration (including XML) loadable without rebuilding firmware and executed by a controller of the medical device, and wherein authoring or editing of the sequence of functional elements is performed by the configuration module.

10. The method according to claim 8, including using a system of medical devices including at least two medical devices connected to one another to exchange data and/or control signals, wherein at least one of the medical devices is a defibrillator or a ventilator, wherein the at least one medical device comprises: at least one control unit; a storage device; and a display for displaying a graphic user interface, wherein the medical device is constructed to be configurable by a configuration module that is executable independently of the medical device to be configured, wherein configuring the medical device includes adjusting and/or creating operating modes of the medical device and wherein a process of the control of the medical device is defined in each case by an operating mode, and wherein a configuration created by an operator and tested using a device simulation is loadable onto the medical device manually or by using an update server, wherein the configuration is a declarative configuration (including XML) loadable without rebuilding firmware and executed by a controller of the medical device, and wherein authoring or editing of the sequence of functional elements is performed by the configuration module.

* * * * *